US011471433B1

(12) United States Patent
Martinez et al.

(10) Patent No.: US 11,471,433 B1
(45) Date of Patent: Oct. 18, 2022

(54) POSTBIOTIC COMPOSITIONS AND RELATED METHODS FOR AGRICULTURE

(71) Applicant: Flagship Pioneering Innovations V, Inc., Cambridge, MA (US)

(72) Inventors: Ignacio Martinez, Lexington, MA (US); Maier Steve Avendano Amado, Cambridge, MA (US); Thomas Michael Malvar, North Stonington, CT (US); Emily Michelle Mallick, Millbury, MA (US)

(73) Assignee: Flagship Pioneering Innovations V, Inc., Cambridge, MA (US)

( * ) Notice: Subject to any disclaimer, the term of this patent is extended or adjusted under 35 U.S.C. 154(b) by 0 days.

(21) Appl. No.: 16/944,799

(22) Filed: Jul. 31, 2020

Related U.S. Application Data

(60) Provisional application No. 62/881,723, filed on Aug. 1, 2019.

(51) Int. Cl.
| | | |
|---|---|---|
| A23K 20/158 | (2016.01) | |
| A61K 31/19 | (2006.01) | |
| A61K 9/00 | (2006.01) | |
| A23K 10/18 | (2016.01) | |
| A23K 50/90 | (2016.01) | |

(52) U.S. Cl.
CPC .............. *A61K 31/19* (2013.01); *A23K 10/18* (2016.05); *A23K 20/158* (2016.05); *A23K 50/90* (2016.05); *A61K 9/0053* (2013.01)

(58) Field of Classification Search
None
See application file for complete search history.

(56) References Cited

U.S. PATENT DOCUMENTS

| | | | |
|---|---|---|---|
| 8,334,366 B1 | 12/2012 | Hughes et al. | |
| 10,086,024 B2 | 10/2018 | Kovarik | |
| 2008/0295207 A1 | 11/2008 | Baum et al. | |
| 2009/0162482 A1* | 6/2009 | Wardell | A23L 33/185 426/62 |
| 2009/0285937 A1 | 11/2009 | Vadis et al. | |
| 2011/0145939 A1 | 6/2011 | O'Neill | |
| 2011/0150780 A1 | 6/2011 | Krieger et al. | |
| 2011/0209228 A1 | 8/2011 | Cocks et al. | |
| 2011/0229937 A1 | 9/2011 | Pompejus et al. | |
| 2011/0263487 A1 | 10/2011 | Meagher | |
| 2014/0349917 A1 | 11/2014 | Eckert et al. | |
| 2017/0015716 A1 | 1/2017 | Walensky et al. | |
| 2019/0015528 A1 | 1/2019 | Moran et al. | |
| 2019/0367943 A1* | 12/2019 | Martinez | C12N 15/113 |

FOREIGN PATENT DOCUMENTS

| | | |
|---|---|---|
| CN | 106472882 A | 3/2017 |
| CN | 106962696 A | 7/2017 |
| CN | 107028037 A | 8/2017 |
| CN | 108782465 A | 11/2018 |
| CN | 108783118 A | 11/2018 |
| CN | 108812552 A | 11/2018 |
| CN | 108813226 A | 11/2018 |
| CN | 109055268 A | 12/2018 |
| EP | 2949220 A1 | 12/2015 |
| FR | 2985664 A1 | 7/2013 |
| KR | 2010-0125747 A | 12/2010 |
| KR | 2012-0123975 A | 11/2012 |
| KR | 2013-0101370 A | 9/2013 |
| MD | 1193 Y | 9/2017 |
| WO | WO-88/00976 A1 | 2/1988 |
| WO | WO-95/16776 A1 | 6/1995 |
| WO | WO-2005/034863 A2 | 4/2005 |
| WO | WO-2008/084074 A2 | 7/2008 |
| WO | WO-2014/097338 A1 | 6/2014 |
| WO | WO-2015/020516 A1 | 2/2015 |
| WO | WO-2015/100432 A2 | 7/2015 |
| WO | WO-2015/191744 A1 | 12/2015 |
| WO | WO-2016/004312 A1 | 1/2016 |
| WO | WO-2018/051344 A1 | 3/2018 |

OTHER PUBLICATIONS

Behgatyan, M. et al. Nutritional Effects of Different Levels of Acetic Acid, Probiotic and Antibiotic on the Performance of Honey Bee. Research in Agricultural Science 3(2)240-251, 2008. English abstract provided. (Year: 2008).*
Iwai, H. et al. Improvement of Artificial Diet for Aphidophagous syrphids ... Applied Entomology and Zoology 44(3)439-446, 2009. (Year: 2009).*
Al-Ghamdi et al., "Effect of gut bacterial isolates from *Apis mellifera jementica* on *Paenibacillus larvae* infected bee larvae," Saudi J Biol Sci. 25(2):383-87 (2018).
Alberoni et al., "Beneficial microorganisms for honey bees: problems and progresses," Appl Microbiol Biotechnol. 100(22):9469-82 (2016).
Alberoni et al., "Impact of beneficial bacteria supplementation on the gut microbiota, colony development and productivity of *Apis mellifera* L.," Beneficial Microbes. 9(2):269-78 (2018).
Amos, "UBC students give bees a chance," University of British Columbia News, <http://news.ubc.ca/2015/09/18/ubc-students-give-bees-a-chance/>, dated Sep. 18, 2015 (3 pages).
Anderson et al., "An emerging paradigm of colony health: microbial balance of the honey bee and hive (*Apis mellifera*)" Insect Soc. 58:431-44 (2011).
Audisio et al., "Effect of *Lactobacillus johnsonii* CRL1647 on different parameters of honeybee colonies and bacterial populations of the bee gut," Benef Microbes. 6(5):687-95 (2015).
Audisio, "Gram-positive bacteria with probiotic potential for the *Apis mellifera* L. honey bee: the experience in the northwest of Argentina," Probiotics & Antimicro Prot. 9(1):22-31 (2017).
Baffoni et al., "Effect of dietary supplementation of *Bifidobacterium* and *Lactobacillus* strains in *Apis mellifera* L. against *Nosema ceranae*," Beneficial Microbes. 7(1):45-51 (2016).
Broderick et al., "Gut-associated microbes of *Drosophila melanogaster*," Gut Microbes. 3(4): 307-321 (2012).
Camiletti et al. "*Drosophila* as a Genetically Tractable Model for Social Insect Behavior," Front Ecol Evol. 4:1-9 (2016).

(Continued)

*Primary Examiner* — Ralph J Gitomer
(74) *Attorney, Agent, or Firm* — Clark & Elbing LLP

(57) ABSTRACT

Disclosed herein are compositions and methods for increasing the fitness of insects for agriculture or commerce, wherein the composition includes a postbiotic agent (e.g., a short chain fatty acid).

21 Claims, No Drawings

(56) References Cited

OTHER PUBLICATIONS

Chan et al., "Changes in protein expression during honey bee larval development," Genome Biol. 9(10):R156 (2008) (14 pages).
Chmiel et al. "Deleterious Effects of Neonicotinoid Pesticides on *Drosophila melanogaster* Immune Pathways," mBio. 10(5): (2019) (14 pages).
Corby-Harris et al., "The bacterial communities associated with honey bee (*Apis mellifera*) foragers," PLoS One. 9(4):e95056 (2014) (13 pages).
Crotti et al., "Microbial symbionts of honeybees: a promising tool to improve honeybee health," N Biotechnol. 30(6):716-22 (2013).
Crotti et al., "Microbial symbionts: a resource for the management of insect-related problems," Microb Biotechnol. 5(3):307-17 (2012).
Daisley et al. "Neonicotinoid-induced pathogen susceptibility is mitigated by *Lactobacillus plantarum* immune stimulation in a *Drosophila melanogaster* model," Sci Rep. 7(1): 2703 (2017) (13 pages).
Dearden et al. "Patterns of conservation and change in honey bee developmental genes," Genome Res. 16(11):1376-1384 (2006).
Dike et al., "Production of L-methionine by Bacillus cereus isolated from different soil eocvars in Owerri, South East Nigeria," Euro J Exp Biol 2(2):311-314 (2012).
Dong et al. "Overproduction of Aromatic Amino Acids from Cyanobacteria," The Summer Undergraduate Research Fellowship (SURF) Symposium, Aug. 2, West Lafayette, IN. (Abstract only) (2018).
Donkersley et al., "Bacterial communites associated wth honeybee food stores are correlated with land use" Ecology and Evolution. 8(10):4743-56 (2018).
Douglas, "The *Drosophila* model for microbiome research," available in PMC Jun. 20, 2019, published in final edited form as: Lab Anim (NY). 47(6):157-164 (2018) (19 pages).
El Khoury et al., "Deleterious interaction between honeybees (*Apis mellifera*) and its microsporidian intracellular parasite *Nosema ceranae* was mitigated by adminstrating either endogenous or allochthonous gut microbiota strains," Front Ecol Evol. 6:58 (2018) (15 pages).
Evans et al., "Bacterial probiotics induce an immune response in the honey bee (Hymenoptera: Apidae)," J Econ Entomol. 97(3):752-6 (2004) (6 pages).
Extended European Search Report for European Patent Application No. 18744047.4 dated Jun. 9, 2020 (7 pages).
Forsgren et al., "Novel lactic acid bacteria inhibiting *Paenibacillus larvae* in honey bee larvae," Apidologie. 41(1):99-108 (2010).
Galang et al. "Analysis of the *Drosophila melanogaster* anti-ovarian response to honey bee queen mandibular pheromone," Insect Mol Biol. 28(1): 99-111 (2019).
Hamdi et al., "Gut microbiome dysbiosis and honeybee health," Journal of Applied Entomology. 135(7):524-533 (2011) (11 pages).
Hütter et al. "Amino Acid Overproduction," Industrial Aspects of Biochemistry and Genetics. 87: 49-59(1985).
International Preliminary Reporton Patentability for PCT Application No. PCT/US2018/015025, dated Jul. 30, 2019 (7 pages).
International Search Report and Written Opinion for International Application No. PCT/US2018/015025, dated Apr. 13, 2018 (13 pages).
International Search Report and Written Opinion for International Application No. PCT/US2018/015077, dated Apr. 23, 2018 (16 pages).
Kaznowski et al., "The effects of probiotic supplementation on the content of intestinal microflora and chemical composition of worker honey bees (*Apis mellifera*)," J Apic Res. 44(1):10-4 (2005) (6 pages).
Kikuchi et al., "Symbiont-mediated insecticide resistance," Proc Natl Acad Sci U.S.A. 109(22):8618-22 (2012).

Kim et al. "Physiological responses of insects to microbial fermentation products: insights from the interactions between *Drosophila* and acetic acid," available in PMC Apr. 1, 2019, published in final edited form as: J Insect Physiol. 106(Pt 1):13-19 (2018) (20 pages).
Liu et al., "Disruption of methionine metabolism in *Drosophila melanogaster* impacts histone methylation and results in loss of viability," G3 (Bethesda). 6(1):121-32 (2015).
McCaughey et al., "Amino Acids and Protein Adequacy for Honey Bees of Pollens from Desert Plants and Other Floral Sources," Apidologie 11 (1): 75-86 (1980).
Mondal et al., "Methionine Production by Microorganisms," Folia Microbiol (Praha). 41(6):465-472 (1996).
Odunfa et al., "Evaluation of lysine and methionine production in some Lactobacilli and yeasts from ogi," Int J Food Microbiol 631 (1-2):159-63 (2001).
Patruica et al., "The effect of using prebiotic and probiotic products on intestinal micro-flora of the honeybee (*Apis mellifera carpatica*)," Bull Entomol Res. 102(6):619-23 (2012).
Ptaszynska et al., "Are commerical probiotics and prebiotics effective in the treatment and prevention of honeybee nosemosis C?," Parasitol Res. 115:397-406 (2016) (11 pages).
Rodriguez et al. "Engineering *Escherichia coli* to overproduce aromatic amino acids and derived compounds," Microb Cell Fact. 13(1):126 (2014) (15 pages).
Sahm et al. "Metabolic design in amino acid producing bacterium *Corynebacterium glutamicum*," FEMS Microbiology Reviews. 16(2-3): 243-52 (1995).
Sanchez et al. "Our microbes not only produce antibiotics, they also overproduce amino acids," J Antibiot. 71: 26-36 (2018).
Sannasi, Inhibition of ovary development of the fruit-fly, *Drosophila melanogaster* by synthetic "queen substance," Life Sci. 8(14): 785-789 (1969).
Santo Domingo et al., "Characterization of the Cricket Hindgut Microbiota with Fluorescently Labeled rRNA-Targeted Oligonucleotide Probes," Appl Environ Microbiol. 64(2):752-5 (1998).
Schneider, "Using *Drosophila* as a model insect," Nat Rev Genet. 1(3):218-26 (2000).
Schwarz et al., "Early gut colonizers shape parasite susceptibility and microbiota composition in honey bee workers," Proc Natl Acad Sci USA. 113(33):9345-50 (2016).
Shapira, "Gut Microbiotas and Host Evolution: Scaling Up Symbiosis," Trends Ecol Evol. 31(7):539-549 (2016).
Sharma et al., "Metabolism of 1-naphthyl-N-methyl carbamate (carbaryl) by bacterial isolates from honey bees and the effect of bacterial inoculations on carbaryl tolerance in bees," J Appl Bacteriol. 81:235-41 (1996).
Shin et al. "*Drosophila* Microbiome Modulates Host Developmental and Metabolic Homeostasis via Insulin Signaling," Science. 334(6056): 670-674 (2011) (6 pages).
Singh et al., "Microbial Degradation of Organophosphorus Compounds," FEMS Microbiol Rev. 30(3):428-71 (2006).
Sokolowski, "Social Interactions in "Simple" Model Systems," Neuron. 65(6): 780-94 (2010).
Storelli et al., "Lactobacillus plantarum Promotes *Drosophila* Systemic Growth by Modulating Hormonal Signals Through TOR-Dependent Nutrient Sensing," Cell Metab. 14(3): 403-414 (2011).
Tower," Lactobacillus plantarum Gives *Drosophila* the Grow Signal," Cell Metab. 14(3): 283-284 (2011).
Trinder et al., "Probiotic Lactobacillus rhamnosus reduces organophosphate pesticide absorption and toxicity to *Drosophila melanogaster*," Applied and Environmental Microbiology (2016) vol. 82, No. 20, pp. 6204-6213.
Trinder et al., "*Drosophila melanogaster* as a High-Throughput Model for Host-Microbiota Interactions," Front Microbiol. 8:751 (2017) (8 pages).
Trotschel et al., "Characterization of methionine export in Corynebacterium glutamicum," J Bacteriol. 187(11):3786-94 (2005).
Zheng et al., "Honeybee Gut Microbiota Promotes Host Weight Gain via Bacterial Metabolism and Hormonal Signaling," Proc Natl Acad Sci USA. 114(18):4775-4780 (2017).

\* cited by examiner

POSTBIOTIC COMPOSITIONS AND RELATED METHODS FOR AGRICULTURE

BACKGROUND

Insects can serve a variety of beneficial roles in agriculture and commerce. For example, certain insects can be in utilized in agriculture for pollination efforts or pest control and in commerce for the production of commercial products, such as honey.

SUMMARY OF THE INVENTION

Disclosed herein are compositions and methods for increasing the fitness of insects for agriculture or commerce, wherein the composition includes a postbiotic agent (e.g., a short chain fatty acid).

In one aspect, provided herein is a method of increasing the fitness of an insect including delivering to the insect a composition including a postbiotic agent.

In some embodiments of the methods herein, the postbiotic agent is one or more short chain fatty acids (SCFAs). In some embodiments, the one or more SCFAs is acetate, propionate, and/or butyrate.

In some embodiments of the methods herein, the postbiotic agent is an enzyme, a peptide, a teichoic acid, a muropeptide, a polysaccharide, or an organic acid.

In some embodiments of the methods herein, the postbiotic agent is at least 0.1%, 0.2%, 0.4%, 0.5%, 0.8%, 1%, 2%, 5%, 10%, 20%, 30%, 40%, 50%, 60%, 70%, 80%, or 90% of the composition.

In some embodiments of the methods herein, the insect is a beneficial insect. In some embodiments, the insect is a bee. In some embodiments, the bee is a honeybee. In some embodiments, the honeybee is *Apis mellifera*.

In some embodiments of the methods herein, the insect is utilized in the production of food for humans and/or feed for animals. In some embodiments, the insect is a cricket, cicada, grasshopper, ant, caterpillar, or scorpion. In some embodiments, the insect is developmentally an embryo, larva, pupa, or adult.

In some embodiments of the methods herein, the insect includes its native microbiota prior to delivery of the composition. Alternatively, the insect may be pre-treated with a probiotic microbial agent.

In some embodiments of the methods herein, the method is effective to increase the fitness of the insect relative to an untreated insect. In some embodiments, the increase in fitness is an increase in developmental rate, body size, nutritional profile, or body mass of the insect relative to the untreated insect.

In some embodiments, the increase in fitness is an increase in vitellogenin protein in the insect relative to the untreated insect. In some embodiments, the increase in fitness is an increase in vitellogenin gene expression in the insect relative to the untreated insect.

In some embodiments of the methods herein, the composition is delivered to the insect to at least one habitat where the insect grows, lives, or reproduces.

In some embodiments of the methods herein, the composition is a liquid, a solid, an aerosol, a paste, a gel, or a gas composition.

In some embodiments of the methods herein, the postbiotic agent is formulated in a carrier. In some embodiments, the carrier includes a nanoparticle, or a lipid membrane.

In some embodiments of the methods herein, the postbiotic agent is delivered in an attenuated bacteria for ingestion by the insect. In some embodiments, the postbiotic agent is delivered in a plant for ingestion by the insect.

In some embodiments of the methods herein, the composition is delivered as an insect comestible composition for ingestion by the insect.

In some embodiments of the methods herein, the composition is delivered to the insect by ingestion, infusion, injection, or spraying.

In some embodiments of the methods herein, the composition includes an agriculturally acceptable carrier.

In another aspect, provided herein is a modified insect produced by a method including contacting the insect with a composition including a postbiotic agent in an amount and for a duration sufficient to increase the fitness of the insect relative to an untreated insect.

In some embodiments of the modified insect herein, the postbiotic agent is one or more short chain fatty acids (SCFAs). In some embodiments, the one or more SCFAs is acetate, propionate, and/or butyrate.

In some embodiments of the modified insect herein, the postbiotic agent is an enzyme, a peptide, a teichoic acid, a muropeptide, a polysaccharide, or an organic acid.

In some embodiments of the modified insect herein, the postbiotic agent is at least 0.1%, 0.2%, 0.4%, 0.5%, 0.8%, 1%, 2%, 5%, 10%, 20%, 30%, 40%, 50%, 60%, 70%, 80%, or 90% of the composition.

In some embodiments of the modified insect herein, the insect is a beneficial insect. In some embodiments, the insect is a bee. In some embodiments, the bee is a honeybee (e.g., *Apis mellifera*).

In some embodiments of the modified insect herein, the insect is utilized in the production of food for humans and/or feed for animals. In some embodiments, the insect is a cricket, cicada, grasshopper, ant, caterpillar, or scorpion.

In some embodiments of the modified insect herein, the insect includes its native microbiota prior to delivery of the composition.

In some embodiments of the modified insect herein, the insect is pre-treated with a probiotic microbial agent.

In some embodiments of the modified insect herein, the increase in fitness is an increase in developmental rate, body size, body mass, or nutritional profile of the insect relative to the untreated insect. In some embodiments, the increase in fitness is an increase in vitellogenin protein in the insect relative to the untreated insect. In some embodiments, the increase in fitness is an increase in vitellogenin gene expression in the insect relative to the untreated insect.

In some embodiments of the modified insect herein, the composition is delivered to the insect to at least one habitat where the insect grows, lives, or reproduces.

In some embodiments of the modified insect herein, the composition is a liquid, a solid, an aerosol, a paste, a gel, or a gas composition.

In some embodiments of the modified insect herein, the postbiotic agent is formulated in a carrier. In some embodiments, the carrier includes a nanoparticle, or a lipid membrane.

In some embodiments of the modified insect herein, the postbiotic agent is delivered in an attenuated bacteria for ingestion by the insect. In some embodiments, the postbiotic agent is delivered in a plant for ingestion by the insect.

In some embodiments of the modified insect herein, the composition is delivered as an insect comestible composition for ingestion by the insect.

In some embodiments of the modified insect herein, the composition is delivered to the insect by ingestion, infusion, injection, or spraying.

In some embodiments of the modified insect herein, the composition includes an agriculturally acceptable carrier.

In another aspect, provided herein is a method of increasing the fitness of a bee including delivering to the bee a composition including a postbiotic agent, wherein the method is effective to increase vitellogenin production in the bee relative to an untreated bee. In some embodiments, the postbiotic agent is a short chain fatty acid (SCFA). In some embodiments, the SCFA is acetate, propionate, or butyrate.

In a further aspect, provided herein is a modified bee including a postbiotic agent at a level effective to increase vitellogenin production in the bee relative to an unmodified bee. In some embodiments, the postbiotic agent is a short chain fatty acid (SCFA). In some embodiments, the SCFA is acetate, propionate, or butyrate.

In yet a further aspect, provided herein is a modified bee produced by a method including contacting the bee with a composition including a postbiotic agent in an amount and for a duration sufficient to increase vitellogenin production in the bee relative to an unmodified bee. In some embodiments, the postbiotic agent is a short chain fatty acid (SCFA). In some embodiments, the SCFA is acetate, propionate, or butyrate.

In another aspect, provided herein is a composition including a postbiotic agent and a carrier, wherein the composition is formulated for delivery to an insect, or a habitat thereof.

In some embodiments of the composition herein, the postbiotic agent is one or more short chain fatty acids (SCFAs). In some embodiments, the one or more SCFAs is acetate, propionate, and/or butyrate. In some embodiments, the postbiotic agent is an enzyme, a peptide, a teichoic acid, a muropeptide, a polysaccharide, or an organic acid. In some embodiments, the postbiotic agent is at least 0.1%, 0.2%, 0.4%, 0.5%, 0.8%, 1%, 2%, 5%, 10%, 20%, 30%, 40%, 50%, 60%, 70%, 80%, or 90% of the composition.

In some embodiments of the composition herein, the carrier is a liquid, a solid, an aerosol, a paste, a gel, or a gas composition. In some embodiments, the carrier is a sugar syrup, corn syrup, or honey. In some embodiments, the carrier is a nanoparticle or lipid membrane. In some embodiments, the carrier is an attenuated bacteria.

In some embodiments of the composition herein, the composition is formulated for delivery to the insect by ingestion, infusion, injection, spraying, smoking, or fogging. In some embodiments, the composition is formulated for delivery to at least one habitat where the insect grows, lives, reproduces, or feeds. In some embodiments, the composition is formulated for delivery to a beehive. In some embodiments, the composition is formulated for delivery to a plant ingested by the insect.

In another aspect, provided herein is a modified plant or part thereof including a postbiotic agent, wherein the plant or part thereof is ingested by an insect. In some embodiments, the plant is genetically engineered to produce the postbiotic agent, e.g., by expression from a heterologous genetic construct.

Definitions

As used herein, the term "effective amount" refers to an amount of a postbiotic agent or composition including said agent sufficient to effect the recited result, e.g., to increase or promote the fitness of an insect; to reach a target level (e.g., a predetermined or threshold level) of a postbiotic agent concentration inside a target host; to reach a target level (e.g., a predetermined or threshold level) of a postbiotic agent concentration inside a target host gut; to reach a target level (e.g., a predetermined or threshold level) of a postbiotic agent concentration inside a target host bacteriocyte; or to modulate the fitness of a target host.

As used herein, the term "fitness" refers to the ability of an insect to survive, grow, and/or to produce surviving offspring. Fitness of an insect may be measured by one or more parameters, including, but not limited to, life span, reproductive rate, mobility, body weight, nutritional profile, and/or metabolic rate. Fitness may additionally be measured based on measures of activity (e.g., pollination) or product output (e.g., honey or silk).

As used herein, the term "gut" refers to any portion of an insect's gut, including, the foregut, midgut, or hindgut of the insect.

As used herein, the term "host" refers to an organism (e.g., insect) carrying resident microorganisms (e.g., endogenous microorganisms, endosymbiotic microorganisms (e.g., primary or secondary endosymbionts), commensal organisms, and/or pathogenic microorganisms).

As used herein, "increasing the fitness of an insect" refers to any favorable alteration in insect physiology, phenotype, or any activity of the insect, including, but not limited to, any one or more of the following desired effects: (1) increasing a population of an insect by about 1%, 2%, 3%, 4%, 6%, 7%, 8%, 9%, 10%, 20%, 30%, 40%, 50%, 60%, 70%, 80%, 90%, 95%, 99%, 100% or more; (2) increasing the reproductive rate of an insect by about 1%, 2%, 3%, 4%, 6%, 7%, 8%, 9%, 10%, 20%, 30%, 40%, 50%, 60%, 70%, 80%, 90%, 95%, 99%, 100% or more; (3) increasing the mobility of an insect by about 1%, 2%, 3%, 4%, 6%, 7%, 8%, 9%, 10%, 20%, 30%, 40%, 50%, 60%, 70%, 80%, 90%, 95%, 99%, 100% or more; (4) increasing the body weight of an insect by about 1%, 2%, 3%, 4%, 6%, 7%, 8%, 9%, 10%, 20%, 30%, 40%, 50%, 60%, 70%, 80%, 90%, 95%, 99%, 100% or more; (5) increasing the metabolic rate or activity of an insect by about 1%, 2%, 3%, 4%, 6%, 7%, 8%, 9%, 10%, 20%, 30%, 40%, 50%, 60%, 70%, 80%, 90%, 95%, 99%, 100% or more; (6) increasing pollination (e.g., number of plants pollinated in a given amount of time) by an insect by about 1%, 2%, 3%, 4%, 6%, 7%, 8%, 9%, 10%, 20%, 30%, 40%, 50%, 60%, 70%, 80%, 90%, 95%, 99%, 100% or more; (7) increasing production of insect byproducts (e.g., honey or silk) by about 1%, 2%, 3%, 4%, 6%, 7%, 8%, 9%, 10%, 20%, 30%, 40%, 50%, 60%, 70%, 80%, 90%, 95%, 99%, 100% or more; (8) increasing nutrient content of the insect (e.g., protein, fatty acids, or amino acids) by about 1%, 2%, 3%, 4%, 6%, 7%, 8%, 9%, 10%, 20%, 30%, 40%, 50%, 60%, 70%, 80%, 90%, 95%, 99%, 100% or more; or (9) increasing insect resistance to pesticides by about 1%, 2%, 3%, 4%, 6%, 7%, 8%, 9%, 10%, 20%, 30%, 40%, 50%, 60%, 70%, 80%, 90%, 95%, 99%, 100% or more. An increase in insect fitness can be determined in comparison to a control (e.g., an untreated insect).

As used herein, "increasing a nutritional profile of an insect" refers to increased production of a nutrient that may increase protein content, body mass, and/or overall nutritional value of the insect.

The term "insect" or "arthropod" includes any organism belonging to the phylum Arthropoda and to the class Insecta or the class Arachnida, in any stage of development, i.e., immature or adult insects. As used herein, the term "beneficial insect" refers to an insect whose presence confers benefits to agricultural, horticultural, or commercial applications, or whose presence or activity is otherwise desirable.

As used herein, the term "microorganism" refers to bacteria or fungi. Microorganisms may refer to microorganisms resident in an insect (e.g., endogenous microorganisms, endosymbiotic microorganisms (e.g., primary or secondary endosymbionts)) or microorganisms exogenous to the insect, including those that produce postbiotic agents.

As used herein, the term "native microbiota" refers to the microorganisms that reside in an untreated insect (e.g., an insect that has not been treated with an agent or procedure that alters the microbiome of the insect (e.g., an antiseptic, an antibiotic, a prebiotic, a probiotic, or a postbiotic agent; or an irradiation procedure)).

As used herein, the term "postbiotic agent" refers to non-viable agents capable of being produced by bacteria (e.g., prebiotic bacteria) or byproducts thereof, including compounds secreted by live bacteria or released after bacterial lysis, such as metabolites, enzymes, peptides, teichoic acids, peptidoglycan-derived muropeptides, polysaccharides, cell surface proteins, or organic acids. For example, the postbiotic may be one or more short chain fatty acids (e.g., acetate, propionate, and/or butyrate).

As used herein, the term "peptide," "protein," or "polypeptide" encompasses any chain of naturally or non-naturally occurring amino acids (either D- or L-amino acids), regardless of length (e.g., at least 2, 3, 4, 5, 6, 7, 10, 12, 14, 16, 18, 20, 25, 30, 40, 50, 100, or more amino acids), the presence or absence of post-translational modifications (e.g., glycosylation or phosphorylation), or the presence of, e.g., one or more non-amino acyl groups (for example, sugar, lipid, etc.) covalently linked to the peptide, and includes, for example, natural proteins, synthetic, or recombinant polypeptides and peptides, hybrid molecules, peptoids, or peptidomimetics.

As used herein, "percent identity" between two sequences is determined by the BLAST 2.0 algorithm, which is described in Altschul et al. (*J. Mol. Biol.* 215:403-410, 1990). Software for performing BLAST analyses is publicly available through the National Center for Biotechnology Information.

As used herein, the term "plant" refers to whole plants, plant organs, plant tissues, seeds, plant cells, seeds, and progeny of the same. Plant cells include, without limitation, cells from seeds, suspension cultures, embryos, meristematic regions, callus tissue, leaves, roots, shoots, gametophytes, sporophytes, pollen, or microspores. Plant parts include differentiated or undifferentiated tissues including, but not limited to the following: roots, stems, shoots, leaves, pollen, seeds, tumor tissue, and various forms of cells and culture (e.g., single cells, protoplasts, embryos, or callus tissue). The plant tissue may be in a plant or in a plant organ, tissue, or cell culture.

As used herein, the term "probiotic microbial agent" refers to live microorganisms, such as non-pathogenic microbes, which, when administered in sufficient amounts to an insect, promote the fitness of the insect.

As used herein, the term "untreated insect" or "unmodified insect" refers to an insect, or population thereof, that has not been specifically contacted with or delivered (e.g., in accordance with a method described herein) a postbiotic agent (e.g., has not been contacted with or delivered a postbiotic agent at any point in time, or has been assessed at a point in time prior to contact with or delivery of the postbiotic agent).

Other features and advantages of the invention will be apparent from the following Detailed Description and the Claims.

DETAILED DESCRIPTION

Provided herein are methods and compositions including a postbiotic agent for use in increasing the fitness of an insect, particularly a variety of beneficial insects, such as bees and silkworms, utilized in agriculture and commerce, such as crickets, cicadas, grasshoppers, ants, insect larvae, caterpillars, and scorpions, utilized in the production of food and feed for humans and animals, respectively. Postbiotic agents refer to non-viable agents capable of being produced by bacteria (e.g., prebiotic bacteria) or byproducts thereof, including compounds secreted by live bacteria or released after bacterial lysis, such as metabolites, enzymes, peptides, teichoic acids, peptidoglycan-derived muropeptides, polysaccharides, cell surface proteins, or organic acids. For example, the postbiotic may be one or more short chain fatty acids (e.g., acetate, propionate, and/or butyrate). Postbiotics possess different functional properties including, but not limited to, antimicrobial, antioxidant, and immunomodulatory. These properties can positively affect the microbiota homeostasis and/or the host metabolic and signaling pathways, thus affecting specific physiological, immunological, neuro-hormone, biological, regulatory, or metabolic reactions of the insects treated with a postbiotic agent, as described herein.

I. Methods of Increasing Insect Fitness

Provided herein are methods of modifying (e.g., increasing the fitness) of an insect by delivering to the insect a composition including a postbiotic agent. Examples of insects that can benefit from the present methods, fitness benefits that can be conferred by the present methods, and of methods for delivering the postbiotic agent are further described, below.

i. Insects

The postbiotic agents herein can be applied to a variety of insects. For example, the insect may be a beneficial insect, such as a plant pollinator, a natural competitor of a pest, or a producer of useful substances for humans or animals. The term "beneficial insect" as used herein, refers to an insect that confers a benefit (e.g., economical and/or ecological) to humans, animals, an ecosystem, and/or the environment. For example, the insect may be an insect that is involved in the production of a commercial product, including, but not limited to, insects cultivated to produce food (e.g., honey from honey bees, e.g., *Apis mellifera*), materials (such as silk from *Bombyx mori*), and/or substances (e.g., lac from *Laccifer lacca* or pigments from *Dactylopius* coccus and Cynipidae). In some instances, the insect may be harvested, or one or more parts of the insect may be harvested, and processed for use in the manufacture of a consumable product, including any product safe for human or animal consumption (e.g., ingestion). Additionally, the insect may include insects that are used in agricultural applications, including insects that aid in the pollination of crops, spreading seeds, or pest control. Further, in some instances, the insect may be an insect that is useful for waste disposal and/or organic recycling (e.g., earthworms, termites, or Diptera larvae). The insect may be one that has its native (i.e., unaltered) microbiota. Alternatively, the insect may be one that has received probiotic compositions prior to or during delivery of the postbiotic agent.

In some instances, the insect may be harvested and distributed in a whole form (e.g., as the whole, unprocessed insect) as a consumable product. In some instances, the whole harvested insect is processed (e.g., ground up) and distributed as a consumable product. Alternatively, one or more parts of the insect (e.g., one or more body parts or one or more substances) may be extracted from the insect for use in the manufacture of a consumable product. In some instances, the insect may be a moth, butterfly, fly, cricket, grasshopper, locust, spider, or beetle. In some instances, an insect species is selected based upon their natural nutritional profile or nutrient content. Examples of nutrients include vitamins, carbohydrates, amino acids, polypeptides, or fatty acids.

In some instances, the insect produces a useable product (e.g., honey, silk, beeswax, or shellac). In some instances, the insect is a bee. Exemplary bee genera include, but are not limited to *Apis, Bombus, Trigona*, and *Osmia*. In some instances, the bee is a honeybee (e.g., an insect belonging to the genus *Apis*). In some instances, the honeybee is the species *Apis mellifera* (the European or Western honey bee), *Apis cerana* (the Asiatic, Eastern, or Himalayan honey bee), *Apis dorsata* (the "giant" honey bee), *Apis florea* (the "red dwarf" honey bee), *Apis andreniformis* (the "black dwarf" honey bee), or *Apis nigrocincta*. In some instances, the insect is a silkworm. The silkworm may be a species in the family Bombycidae or Saturniidae.

In some instances, the silkworm is *Bombyx mori*. In some instances, the insect is a lac bug. The lac bug may be a species in the family Kerriidae. In some instances, the lac bug is *Kerria lacca*.

In some instances, the insect aids in pollination of a plant (e.g., bees, beetles, wasps, flies, butterflies, or moths). In some examples, the insect aiding in pollination of a plant is beetle. In some instances, the beetle is a species in the family Buprestidae, Cantharidae, Cerambycidae, Chrysomelidae, Cleridae, Coccinellidae, Elateridae, Melandryidae, Meloidae, Melyridae, Mordellidae, Nitidulidae, Oedemeridae, Scarabaeidae, or Staphyllinidae. In some instances, the insect aiding in pollination of a plant is a butterfly or moth (e.g., Lepidoptera). In some instances, the butterfly or moth is a species in the family Geometridae, Hesperiidae, Lycaenidae, Noctuidae, Nymphalidae, Papilionidae, Pieridae, or Sphingidae. In some instances, the insect aiding in pollination of a plant is a fly (e.g., Diptera). In some instances, the fly is in the family Anthomyiidae, Bibionidae, Bombyffidae, Calliphoridae, Cecidomiidae, Certopogonidae, Chrionomidae, Conopidae, Culicidae, Dolichopodidae, Empididae, Ephydridae, Lonchopteridae, Muscidae, Mycetophilidae, Phoridae, Simuliidae, Stratiomyidae, or Syrphidae. In some instances, the insect aiding in pollination is an ant (e.g., Formicidae), sawfly (e.g., Tenthredinidae), or wasp (e.g., Sphecidae or Vespidae). In some instances, the insect aiding in pollination of a plant is a bee. In some instances, the bee is in the family Andrenidae, Apidae, Colletidae, Halictidae, or Megachilidae.

In some instances, the insect aids in pest control. For example, the insect aiding in pest control may be a species belonging to the family Braconidae (e.g., parasitoid wasps), Carabidae (e.g., ground beetles), Chrysopidae (e.g., green lacewings), Coccinellidae (e.g., ladybugs), Hemerobiidae (e.g., brown lacewings), Ichneumonidae (e.g., ichneumon wasps), Lampyridae (e.g., fireflies), Mantidae (e.g., praying mantises), Myrmeleontidae (e.g., antlions), Odonata (e.g., dragonflies and damselflies), or Syrphidae (e.g., hoverfly). In other instances, the insect aiding in pest control is an insect that competes with an insect that is considered a pest (e.g., an agricultural pest). For example, the Mediterranean fruit fly, *Ceratitis capitata* is a common pest of fruits and vegetables worldwide. One way to control *C. capitata* is to release the sterilized male insect into the environment to compete with wild males to mate the females. In these instances, the insect may be a sterilized male belonging to a species that is typically considered a pest.

In some instances, the insect aids in degradation of waste or organic material. In some examples, the insect aiding in degradation of waste or organic material belongs to Coleoptera or Diptera. In some instances, the insect belonging to Diptera is in the family Calliphoridae, Curtonotidae, Drosophilidae, Fanniidae, Heleomyzidae, Milichiidae, Muscidae, Phoridae, Psychodidae, Scatopsidae, Sepsidae, Sphaeroceridae, Stratiomyidae, Syrphidae, Tephritidae, or Ulidiidae. In some instances, the insect belonging to Coleoptera is in the family Carabidae, Hydrophilidae, Phalacaridae, Ptiliidae, or Staphylinidae.

In particular instances, the postbiotic agents disclosed herein may be used to increase the fitness of a honeybee. In particular instances, the postbiotic agents disclosed herein may be used to increase a nutritional profile of an insect.

ii. Insect Fitness

The present methods are may be effective to confer a variety of fitness benefits to insects. For example, the increase in insect fitness may manifest as an improvement in the physiology of the insect (e.g., improved health or survival, or increased nutritional profile) as a consequence of administration of the postbiotic agent. The fitness of the insect may be measured by one or more parameters, including, but not limited to, reproductive rate, lifespan, mobility, fecundity, body weight, nutritional profile, metabolic rate or activity, or survival in comparison to an insect to which the postbiotic agent has not been administered. In some instances, the postbiotic agent may increase the fitness of the insect in a transient manner. Alternatively, the postbiotic agent may increase the fitness of the insect for the duration of the insect's lifespan.

For example, the methods or compositions provided herein may be effective to improve the overall health of the insect or to improve the overall survival of the insect in comparison to an insect to which the postbiotic agent has not been administered. In some instances, the improved survival of the insect is about 2%, 5%, 10%, 20%, 30%, 40%, 50%, 60%, 70%, 80%, 90%, 100%, or greater than 100% greater relative to a reference level (e.g., a level found in an insect that does not receive a postbiotic agent).

In some instances, the methods and compositions are effective to increase insect reproduction (e.g., reproductive rate) in comparison to an insect to which the postbiotic agent has not been administered. In some instances, the methods and compositions are effective to increase other physiological parameters, such as mobility, body weight, life span, fecundity, or metabolic rate, by about 2%, 5%, 10%, 20%, 30%, 40%, 50%, 60%, 70%, 80%, 90%, 100%, or greater than 100% relative to a reference level (e.g., a level found in an insect that does not receive a postbiotic agent).

In some instances, the increase in insect fitness may manifest as an increased production of a product generated by said insect in comparison to an insect to which the postbiotic agent has not been administered. In some instances, the methods or compositions provided herein may be effective to increase the production of a product generated by the insect, as described herein (e.g., honey, beeswax, beebread, propolis, silk, or lac), by about 2%, 5%, 10%, 20%, 30%, 40%, 50%, 60%, 70%, 80%, 90%, 100%, or greater than 100% relative to a reference level (e.g., a level found in an insect that does not receive a postbiotic agent).

For example, the methods or compositions provided herein may be effective to improve the nutritional profile of the insect or to improve the overall nutrient content (e.g., vitamin, carbohydrate, amino acid, polypeptide, or fatty acid content) of the insect in comparison to an insect to which the postbiotic agent has not been administered. In some instances, the improved nutritional profile or nutrient content of the insect is about 2%, 5%, 10%, 20%, 30%, 40%, 50%, 60%, 70%, 80%, 90%, 100%, or greater than 100% greater relative to a reference level (e.g., a level found in an insect that does not receive a postbiotic agent). In some instances, the increase in insect fitness may manifest as an increase in the frequency or efficacy of a desired activity carried out by the insect (e.g., pollination, predation on pests, seed spreading, or breakdown of waste or organic material) in comparison to an insect to which the postbiotic agent has not been administered. In some instances, the methods or compositions provided herein may be effective to increase the frequency or efficacy of a desired activity carried out by the insect (e.g., pollination, predation on pests, seed spreading, or breakdown of waste or organic material) by about 2%, 5%, 10%, 20%, 30%, 40%, 50%, 60%, 70%, 80%, 90%, 100%, or greater than 100% relative to a reference level (e.g., a level found in an insect that does not receive a postbiotic agent).

In some instances, the increase in insect fitness may manifest as an increase in the production of one or more nutrients in the insect (e.g., vitamins, carbohydrates, amino acids, or polypeptides) in comparison to an insect to which the postbiotic agent has not been administered. In some instances, the methods or compositions provided herein may be effective to increase the production of nutrients in the insect (e.g., vitamins, carbohydrates, amino acids, or polypeptides) by about 2%, 5%, 10%, 20%, 30%, 40%, 50%, 60%, 70%, 80%, 90%, 100%, or greater than 100% relative to a reference level (e.g., a level found in an insect that does not receive a postbiotic agent). In some instances, the methods or compositions provided herein may increase nutrients in the insect by increasing the production of nutrients by one or more microorganisms (e.g., endosymbiont) in the insect.

In some instances, the increase in insect fitness may manifest as a decrease in the insect's sensitivity to a pesticidal agent and/or an increase in the insect's resistance to a pesticidal agent in comparison to an insect to which the postbiotic agent has not been administered. In some instances, the methods or compositions provided herein may be effective to decrease the insect's sensitivity to a pesticidal agent by about 2%, 5%, 10%, 20%, 30%, 40%, 50%, 60%, 70%, 80%, 90%, 100%, or greater than 100% relative to a reference level (e.g., a level found in an insect that does not receive a postbiotic agent). In some instances, the insect's sensitivity to the pesticidal agent is altered by administering a postbiotic agent that degrades a pesticidal agent (e.g., pesticidal-degrading bacteria, e.g., a neonicotinoid-degrading bacteria or an organophosphorus insecticide-degrading bacteria). The pesticidal agent may be any pesticidal agent known in the art, including insecticidal agents. In some instances, the pesticidal agent is a neonicotinoid (e.g., imidacloprid) or an organophosphorus insecticide (e.g., a phosphorothioate, e.g., fenitrothion). In some instances, the methods or compositions provided herein may decrease the insect's sensitivity to a pesticidal agent by increasing the insect's ability to metabolize or degrade the pesticidal agent into usable substrates.

In some instances, the increase in insect fitness may manifest as a decrease in the insect's sensitivity to an allelochemical agent and/or an increase in the insect's resistance to an allelochemical agent in comparison to an insect to which the postbiotic agent has not been administered. In some instances, the methods or compositions provided herein may be effective to increase the insect's resistance to an allelochemical agent by about 2%, 5%, 10%, 20%, 30%, 40%, 50%, 60%, 70%, 80%, 90%, 100%, or greater than 100% relative to a reference level (e.g., a level found in an insect that does not receive a postbiotic agent).

In some instances, the allelochemical agent is caffeine, soyacystatin N, monoterpenes, diterpene acids, or phenolic compounds. In some instances, the methods or compositions provided herein may decrease the insect's sensitivity to an allelochemical agent by increasing the insect's ability to metabolize or degrade the allelochemical agent into usable substrates.

In some instances, the methods or compositions provided herein may be effective to increase the insect's resistance to parasites or pathogens (e.g., fungal, bacterial, or viral pathogens; or parasitic mites (e.g., *Varroa destructor* mite in honeybees)) in comparison to an insect to which the postbiotic agent has not been administered. In some instances, the methods or compositions provided herein may be effective to increase the insect's resistance to a pathogen or parasite (e.g., fungal, bacterial, or viral pathogens; or parasitic mites (e.g., *Varroa destructor* mite in honeybees)) by about 2%, 5%, 10%, 20%, 30%, 40%, 50%, 60%, 70%, 80%, 90%, 100%, or greater than 100% relative to a reference level (e.g., a level found in an insect that does not receive a postbiotic agent).

In some instances, the increase in insect fitness may manifest as other fitness advantages, such as improved tolerance to certain environmental factors (e.g., a high or low temperature tolerance), improved ability to survive in certain habitats, or an improved ability to sustain a certain diet (e.g., an improved ability to metabolize soy vs corn) in comparison to an insect to which the postbiotic agent has not been administered. In some instances, the methods or compositions provided herein may be effective to increase insect fitness in any plurality of ways described herein. Further, the postbiotic agent may increase insect fitness in any number of insect classes, orders, families, genera, or species (e.g., 1 insect species, 2, 3, 4, 5, 6, 7, 8, 9, 10, 15, 20, 30, 40, 50, 60, 70, 80, 90, 100, 150, 200, 200, 250, 500, or more insect species). In some instances, the postbiotic agent acts on a single insect class, order, family, genus, or species.

In some embodiments of the methods herein, the method is effective to increase the fitness of the insect relative to an untreated insect. In some embodiments, the increase in fitness is an increase in developmental rate, body size, body mass, of the insect relative to an untreated insect. In some embodiments, the increase in fitness is an increase in vitellogenin protein in the insect relative to an untreated insect. In some embodiments, the increase in fitness is an increase in vitellogenin gene expression in the insect relative to an untreated insect.

Insect fitness may be evaluated using any standard methods in the art. In some instances, insect fitness may be evaluated by assessing an individual insect. Alternatively, insect fitness may be evaluated by assessing an insect population. For example, an increase in insect fitness may manifest as an increase in successful competition against other insects, thereby leading to an increase in the size of the insect population.

iii. Insects in Agriculture

By increasing the fitness of beneficial insects, the postbiotic agents provided herein may be effective to promote the growth of plants that benefit from said insects. The postbiotic agent may be delivered using any formulations and delivery methods described herein, in an amount and for a duration effective to increase the fitness of the insects of interest and thereby benefit the plant (e.g., increase crop growth, increase crop yield, decrease pest infestation, and/or decrease damage to plants). This may or may not involve direct application of the postbiotic agent to the plant. For example, in instances where the primary insect habitat is different than the region of plant growth, the postbiotic agent may be applied to either the primary insect habitat, the plants of interest, or a combination of both.

In some instances, the plant may be an agricultural crop, such as a cereal, grain, legume, fruit, or vegetable crop. The compositions described herein may be delivered to the crop any time prior to or after harvesting the cereal, grain, legume, fruit, or vegetable. Crop yield is a measurement often used for, e.g., a cereal, grain, or legume and is normally measured in metric tons per hectare (or kilograms per hectare). Crop yield can also refer to the actual seed generation from the plant. In some instances, the postbiotic agent may be effective to increase crop yield (e.g., increase metric tons of cereal, grain, legume, fruit, or vegetable per hectare and/or increase seed generation) by about 2%, 5%, 10%, 20%, 30%, 40%, 50%, 60%, 70%, 80%, 90%, 100%, or more in comparison to a reference level (e.g., a crop to which the postbiotic agent has not been administered.

In some instances, the plant (e.g., crop) may be at risk of developing a pest infestation (e.g., by an insect) or may have already developed a pest infestation. The methods and compositions described herein may be used to reduce or prevent pest infestation in such crops by promoting the fitness of beneficial insects that prey on agricultural pests. In some instances, the postbiotic agent may be effective to reduce crop infestation (e.g., reduce the number of plants infested, reduce the pest population size, or reduce damage to plants) by about 2%, 5%, 10%, 20%, 30%, 40%, 50%, 60%, 70%, 80%, 90%, 100%, or more in comparison to a reference level (e.g., a crop to which the postbiotic agent has not been administered). In other instances, the postbiotic agent may be effective to prevent or reduce the likelihood of crop infestation by about 2%, 5%, 10%, 20%, 30%, 40%, 50%, 60%, 70%, 80%, 90%, 100%, or more in comparison to a reference level (e.g., a crop to which the postbiotic agent has not been administered).

Any suitable plant tissues may benefit from the compositions and methods described herein, including, but not limited to, somatic embryos, pollen, leaves, stems, calli, stolons, microtubers, and shoots. The methods described herein may include treatment of angiosperm and gymnosperm plants such as acacia, alfalfa, apple, apricot, artichoke, ash tree, asparagus, avocado, banana, barley, beans, beet, birch, beech, blackberry, blueberry, broccoli, brussels sprouts, cabbage, canola, cantaloupe, carrot, cassava, cauliflower, cedar, a cereal, celery, chestnut, cherry, Chinese cabbage, citrus, clementine, clover, coffee, corn, cotton, cowpea, cucumber, cypress, eggplant, elm, endive, eucalyptus, fava beans, fennel, figs, fir, geranium, grape, grapefruit, groundnuts, ground cherry, gum hemlock, hickory, kale, kiwifruit, kohlrabi, larch, lettuce, leek, lemon, lime, locust, pine, maidenhair, maize, mango, maple, melon, millet, mushroom, mustard, nuts, oak, oats, okra, onion, orange, an ornamental plant or flower or tree, papaya, palm, parsley, parsnip, pea, peach, peanut, pear, peat, pepper, persimmon, pigeon pea, pine, pineapple, plantain, plum, pomegranate, potato, pumpkin, radicchio, radish, rapeseed, raspberry, rice, rye, sorghum, sallow, soybean, spinach, spruce, squash, strawberry, sugarbeet, sugarcane, sunflower, sweet potato, sweet corn, tangerine, tea, tobacco, tomato, trees, triticale, turf grasses, turnips, a vine, walnut, watercress, watermelon, wheat, yams, yew, and zucchini.

iv. Application Methods

An insect described herein can be exposed to any of the compositions described herein in any suitable manner that permits delivering or administering the composition to the insect. The postbiotic agent may be delivered either alone or in combination with other active (e.g., probiotic agents) or inactive substances and may be applied by, for example, spraying, injection (e.g., microinjection), fogs, through plants, pouring, dipping, in the form of concentrated liquids, gels, solutions, suspensions, sprays, powders, pellets, briquettes, bricks and the like, formulated to deliver an effective concentration of the postbiotic agent. Amounts and locations for application of the compositions described herein are generally determined by the habitat of the insect, the lifecycle stage at which the insect can be targeted by the postbiotic agent, the site where the application is to be made, and the physical and functional characteristics of the postbiotic agent.

In some instances, the composition is delivered directly onto an insect's habitat, e.g., a beehive, by e.g., fogging, smoking, spraying/dusting etc. For example, formulated postbiotic agents can be applied as a smoke or fog or other hive treatment.

In some instances, the composition is sprayed directly onto a plant e.g., crops, by e.g., backpack spraying, aerial spraying, crop spraying/dusting etc. In instances where the postbiotic agent is delivered to a plant, the plant receiving the postbiotic agent may be at any stage of plant growth. For example, formulated postbiotic agents can be applied as a seed-coating or root treatment in early stages of plant growth or as a total plant treatment at later stages of the crop cycle. In some instances, the postbiotic agent may be applied as a topical agent to a plant.

Further, the postbiotic agent may be applied (e.g., in the soil in which a plant grows, or in the water that is used to water the plant) as a systemic agent that is absorbed and distributed through the tissues of a plant. In some instances, plants or food organisms may be genetically transformed to express the postbiotic agent. For example, in some instances, the postbiotic agent is delivered in a modified plant for ingestion by the insect. Alternatively, the postbiotic agent may be delivered in an attenuated bacteria or modified bacteria for ingestion by the insect.

Delayed or continuous release can also be accomplished by coating the postbiotic agent or a composition with the postbiotic agent(s) with a dissolvable or bioerodable coating layer, such as gelatin, which coating dissolves or erodes in the environment of use, to then make the postbiotic agent available, or by dispersing the agent in a dissolvable or erodable matrix. Such continuous release and/or dispensing means devices may be advantageously employed to consistently maintain an effective concentration of one or more of the postbiotic agents described herein.

In some instances, the postbiotic agent may be recommended for field application as an amount of agent per hectare (g/ha or kg/ha) or the amount of active ingredient (e.g., postbiotic agent) per hectare (kg a.i./ha or g a.i./ha). Postbiotic agents of the invention can be applied at a variety of amounts per hectare, for example at about 0.0001, 0.001, 0.005, 0.01, 0.1, 1, 2, 10, 100, 1,000, 2,000, 5,000 (or any range between about 0.0001 and 5,000) kg/ha. For example, about 0.0001 to about 0.01, about 0.01 to about 10, about 10 to about 1,000, about 1,000 to about 5,000 kg/ha.

In some instances where the postbiotic agent is delivered to an insect can be simply "soaked" or "sprayed" with a solution including the postbiotic agent. In other instances, the postbiotic agents may be administered to the insect by oral ingestion, but may also be administered by means which permit penetration through the cuticle or penetration of the insect's respiratory system. For example, the postbiotic agent can be linked to a food component (e.g., comestible) of the insect for ease of delivery and/or in order to increase uptake of the postbiotic agent by the insect. Methods for oral introduction include, for example, directly mixing a postbiotic agent with the insect's food, spraying the postbiotic agent in the insect's habitat or field, as well as engineered approaches in which a species that is used as food is engineered to express a postbiotic agent, then fed to the insect to be affected. In some instances, for example, the postbiotic agent can be incorporated into, or overlaid on the top of, the insect's diet. For example, the postbiotic agent can be sprayed onto a field of crops which an insect inhabits.

The postbiotic agent can also be incorporated into the medium in which the insect grows, lives, reproduces, feeds, or infests. For example, a postbiotic agent can be incorporated into a food container, feeding station, protective wrapping, or a hive. For some applications the postbiotic agent may be bound to a solid support for application in powder form or in a trap or feeding station. As an example, for applications where the composition is to be used in a trap or as bait for a particular insect, the compositions may also be bound to a solid support or encapsulated in a time-release material. For example, in instances where the insect is a honeybee, the compositions described herein can be administered by delivering the composition to a honeybee hive or at least one habitat where a honeybee grows, lives, reproduces, or feeds.

II. Postbiotic Agents

Numerous postbiotic agents (e.g., short chain fatty acids) may be used in the compositions and methods described herein to modify an insect (e.g., increase the fitness of an insect) in accordance with the present methods. Postbiotic agents refer to non-viable agents capable of being produced by bacteria (e.g., prebiotic bacteria) or byproducts thereof, including compounds secreted by live bacteria or released after bacterial lysis, such as metabolites, enzymes, peptides, teichoic acids, peptidoglycan-derived muropeptides, polysaccharides, oligosaccharides, fatty acids, glycerolipids, purines, sphingolipids, cell surface proteins, or organic acids. For example, the postbiotic may be one or more short chain fatty acids (e.g., acetate, propionate, and/or butyrate). Postbiotics possess different functional properties. These properties can positively affect the microbiota homeostasis and/or the host metabolic and signaling pathways, thus affecting specific physiological, immunological, neuro-hormone, biological, regulatory, or metabolic reactions.

A postbiotic agent as described herein can be contacted with an insect in an amount and for a time sufficient to: (a) reach a target level (e.g., a predetermined or threshold level) of concentration inside a target insect; and (b) increase the fitness of the target insect. The postbiotic agents discussed hereinafter, such as short chain fatty acids (SCFAs), bacterial enzymes, bacterial peptides, teichoic acids, muropeptides, bacterial polysaccharides, or bacterial organic acids, can be used to increase the fitness of insects, such as bees.

i. Classes of Postbiotic Agents

In general, postbiotic agents can be differentiated either by their elemental composition, i.e., lipids (e.g. butyrate, propionate, dimethyl acetyl-derived plasmalogen), proteins (e.g. lactocepin, p40 molecule), carbohydrates (e.g. galactose-rich polysaccharides, and teichoic acids), vitamins/cofactors (e.g., B-group vitamins), organic acids (e.g., propionic and 3-phenyllactic acid) and complexes molecules such as peptidoglycan-derived muropeptides, lipoteichoic acids, or by their physiological functions, which include, but are not limited to, immunomodulation, anti-inflammatory, hypocholesterolemic, anti-obesogenic, anti-hypertensive, anti-proliferative, and antioxidant effects.

In some instances, the postbiotic agent is a short chain fatty acid (SCFA). SCFAs produced by bacteria can act as signaling molecules by improving, for example, regulation of lipid metabolism, glucose homeostasis and insulin sensitivity, through the activation of receptors such as G protein-coupled receptors (GPRs), thus contributing in the regulation of energy balance while maintaining metabolic homoeostasis. Further, SCFAs can alter metabolic pathways in insects, such as those involved in vitellogenin production.

For example, SCFAs can be used to increase vitellogenin protein in an insect (e.g., bee) relative to an untreated insect (e.g., bee). Accordingly, in some instances, the postbiotic agent is one or more short chain fatty acids (SCFAs). For example, the postbiotic agent may be acetate, propionate, and/or butyrate. In some instances, the postbiotic agent is two or more of acetate, propionate, and/or butyrate. In some instances, the postbiotic agent is acetate, propionate, and butyrate.

In some instances, the postbiotic agent is a peptide (e.g., an enzyme or polypeptide produced by bacteria). In some instances, the enzyme has antioxidant properties. Examples of intracellular bacterial enzymes useful herein, (e.g. as an antioxidant) include glutathione peroxidase (GPx), superoxide dismutase (SOD), nicotinamide adenine dinucleotide (NADH)-oxidase and NADH-peroxidase. Polypeptides may include naturally occurring polypeptides or recombinantly produced variants. For example, the polypeptide may be a functionally active variant of any of the polypeptides described herein with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, e.g., over a specified region or over the entire sequence, to a sequence of a polypeptide described herein or a naturally occurring polypeptide.

In some instances, the postbiotic agent is a polysaccharide (endo-polysaccharide or exo-polysaccharide). For example, exopolysaccharides or components thereof (e.g., uronic acid) can have antioxidant activity. In some instances, the postbiotic agent is a polysaccharide-glycopeptide complex.

In some instances, the postbiotic agent is a cell wall component (e.g., lipoteichoic acid (LTA) or S-layer proteins). For example, the cell wall component can have immunomodulatory properties including LTA and S-layer proteins. Alternatively, the cell wall component may be a muropeptide.

In some instances, the postbiotic agent is a bacterial membrane component. For example, the bacterial membrane component may be plasmalogen.

In some instances, the postbiotic agent is an organic acid (e.g., propionic acid or 3-pheynyllactic acid).

In some instances, the postbiotic agent contains a mixture of postbiotic agents. The composition including the postbiotic agent may include any number or type (e.g., classes) of postbiotic agents, such as at least about any one of 1 postbiotic agent, 2, 3, 4, 5, 10, 15, 20, or more postbiotic agents. For example, the postbiotic agent can be a bacterial lysate containing a heterogeneous mixture of bacterial compounds (e.g., cell-free supernatants following lysis of bacteria). In some instances, the postbiotic agent can be a cell-free supernatant containing secreted elements from a bacterial cell. In other instances, the postbiotic agent can be a purified from a bacterium. Alternatively, the postbiotic agent may be synthesized based on known postbiotic agents.

The postbiotic agent may be formulated in a composition for any of the uses described herein. A suitable concentration of each postbiotic agent in the composition depends on factors such as efficacy, stability of the postbiotic agent, number of distinct postbiotic agents, the formulation, and methods of application of the composition. Exemplary formulations and compositions including postbiotic agents are described in the section entitled "Formulations and Compositions."

ii. Methods for Obtaining and Identifying Postbiotic Agents

Postbiotics can be obtained using a variety of methods known in the art. For example, postbiotics can be obtained using cell disruption techniques, which include, but are not limited to, heat (Lee et al., *J. of Micro. and Biotech.* 12(3):398-405, 2002; Tejada-Simon & Pestka, *J. of Food Protection.* 62(12):1435-1444, 1999), enzymatic treatments (Li et al., *Food Chem.* 135:1914-1919, 2012), solvent extraction (Kim et al., *Molec. Immun.* 48(4):382-391, 2011), or sonication. Postbiotic agents can be isolated from a variety of bacteria (e.g., gram-negative bacteria or gram-positive bacteria). For example, the postbiotic agent can be isolated from a bacterial strain of *Bifidobacterium* spp., *Lactobacillus* spp., *Lactococcus* spp., or *Streptococcus* spp.

To obtain the postbiotic agent, additional extraction and clean-up steps can be used, such as centrifugation, dialysis, freeze-drying, or column purification. For instance, a chromatography column (e.g., a standard aliphatic hydrophobic interaction chromatography column, e.g., OCTYL-SEPHAROSE® CL-4B column) can be used for isolation of lipoteichoic acid (LTA) from bacteria (e.g., *Lactobacillus johnsonii, L. casei*, or *L. fermentum*; Vidal et al., *Infection and Immunity,* 70(4): 2057-2064, 2002; Matsuguchi et al., *Clin. And Diag. Lab. Immun.,* 10(2), 259-266). Alternatively, dialysis can also be used to extract the postbiotic agent. For example, dialysis can be used to assist the extraction of polysaccharide-glycopeptide complex from bacteria (e.g., *L. casei*; Sawada et al., *Agri. and Bio. Chem.* 54(12):3211-3219, 1990). Further, centrifugation can aid in the extraction of postbiotic agents.

A variety of analytical approaches known in the art can be used for identification of a postbiotic agent. The selection of instrumental technique depends on the analytical goals and the type of characterization (qualitative and/or quantitative) pursued. For example, mass spectrometry (e.g., matrix-assisted laser desorption/ionization time-of-flight (MALDI-TOF) mass spectrometry, Fourier transform ion cyclotron resonance mass spectrometry, or electro-spray ionization mass spectrometry), High Performance Liquid Chromatography (HPLC), Ultra Performance Liquid Chromatography (UPLC) chromatography coupled with tandem mass spectrometry, or spectroscopy (e.g., proton nuclear magnetic resonance spectroscopy (1H-NMR, C-13 NMR) can be used to identify or validate a postbiotic agent for use in accordance with the present methods.

III. Probiotics

In some instances, the methods herein may further include delivering a probiotic to the insect. The probiotic may include, for example, symbiotic bacteria that are beneficial to the insect. For example, bacteria may be provided to promote microbiome development in honey bees, such as *Bartonella apis, Parasaccharibacter apium, Frischella perrara, Snodgrassella alvi, Gilliamela apicola, Bifidobacterium* spp., or *Lactobacillus* spp.

The probiotic may be delivered in combination with or separate from the postbiotic agent. For example, the probiotic may be delivered to the insect prior to the delivery of the postbiotic agent. In other instances, the probiotic may be delivered to the insect in combination with the postbiotic agent. In yet other instances, the probiotic may be delivered to the insect following delivery of the postbiotic agent.

Exemplary bacteria that may be including in the probiotic include, but are not limited to, *Xenorhabdus* spp, *Photorhabdus* spp, *Candidatus* spp, *Buchnera* spp, *Blattabacterium* spp, *Baumania* spp, *Wigglesworthia* spp, *Wolbachia* spp, *Rickettsia* spp, *Orientia* spp, *Sodalis* spp, *Burkholderia* spp, *Cupriavidus* spp, *Frankia* spp, *Snirhizobium* spp, *Streptococcus* spp, *Wolinella* spp, *Xylella* spp, *Erwinia* spp, *Agrobacterium* spp, *Bacillus* spp, *Paenibacillus* spp, *Streptomyces* spp, *Micrococcus* spp, *Corynebacterium* spp, *Acetobacter* spp, *Cyanobacteria* spp, *Salmonella* spp, *Rhodococcus* spp, *Pseudomonas* spp, *Lactobacillus* spp, *Enterococcus* spp, *Alcaligenes* spp, *Klebsiella* spp, *Paenibacillus* spp, *Arthrobacter* spp, *Corynebacterium* spp, *Brevibacterium* spp, *Thermus* spp, *Pseudomonas* spp, *Clostridium* spp, or *Escherichia* spp.

For example, in certain instances, the probiotic includes a bacterium belonging to a *Snodgrassella* spp. (e.g., *Snodgrassella alvi*), a *Gilliamella* spp. (e.g., *Gilliamella apicola*), a *Bartonella* spp. (e.g., *Bartonella apis*), a *Parasaccharibacter* spp. (e.g., *Parasaccharibacter apium*), or a *Lactobacillus* spp. (e.g., *Lactobacillus kunkeei, Lactobacillus* Firm-4) for delivery to an insect (e.g., a bee).

Changes to the populations of bacteria in the insect may be determined by any methods known in the art, such as microarray, polymerase chain reaction (PCR), real-time PCR, flow cytometry, fluorescence microscopy, transmission electron microscopy, fluorescence in situ hybridization (e.g., FISH), spectrophotometry, matrix-assisted laser desorption ionization-mass spectrometry (MALDI-MS), and DNA sequencing. In some instances, a sample of the insect treated with a postbiotic agent is sequenced (e.g., by metagenomics sequencing of 16S rRNA or rDNA) to determine the microbiome of the insect after delivery of the probiotic and/or postbiotic agent. In some instances, a sample of an insect that did not receive the postbiotic agent is also sequenced to provide a reference.

IV. Formulations and Compositions

The compositions described herein may be formulated either in pure form (e.g., the composition contains only the postbiotic agent) or together with one or more additional agents (such as excipient, delivery vehicle, carrier, diluent, stabilizer, etc.) to facilitate application or delivery of the compositions. Examples of suitable excipients and diluents include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline solution, syrup, methylcellulose, methyl- and propylhydroxybenzoates, talc, magnesium stearate, and mineral oil.

To allow ease of application, handling, transportation, storage, and maximum activity, the postbiotic agent can be formulated with other substances. The postbiotic agent can be formulated into, for example, baits, concentrated emulsions, dusts, emulsifiable concentrates, fumigants, gels, granules, microencapsulations, seed treatments, suspension concentrates, suspoemulsions, tablets, water soluble liquids, water dispersible granules or dry flowables, wettable powders, and ultra-low volume solutions.

The postbiotic agent can be applied as aqueous suspensions or emulsions prepared from concentrated formulations of such agents. Such water-soluble, water-suspendable, or emulsifiable formulations are either solids, usually known as wettable powders, or water dispersible granules, or liquids usually known as emulsifiable concentrates, or aqueous suspensions. Wettable powders, which may be compacted to form water dispersible granules, comprise an intimate mixture of the postbiotic agent, a carrier, and surfactants. The carrier is usually selected from among the attapulgite clays, the montmorillonite clays, the diatomaceous earths, or the purified silicates. Effective surfactants, including from about 0.5% to about 10% of the wettable powder, are found among sulfonated lignins, condensed naphthalenesulfonates, naphthalenesulfonates, alkylbenzenesulfonates, alkyl sulfates, and non-ionic surfactants such as ethylene oxide adducts of alkyl phenols.

Emulsifiable concentrates can comprise a suitable concentration of a postbiotic agent, such as from about 50 to about 500 grams per liter of liquid dissolved in a carrier that is either a water miscible solvent or a mixture of water-immiscible organic solvent and emulsifiers. Useful organic solvents include aromatics, especially xylenes and petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are selected from conventional anionic and non-ionic surfactants.

Aqueous suspensions comprise suspensions of a water-insoluble postbiotic agent dispersed in an aqueous carrier at a concentration in the range from about 5% to about 50% by weight. Suspensions are prepared by finely grinding the active agent and vigorously mixing it into a carrier comprised of water and surfactants. Ingredients, such as inorganic salts and synthetic or natural gums may also be added, to increase the density and viscosity of the aqueous carrier.

The postbiotic agent may also be applied as granular compositions that are particularly useful for applications to the soil. Granular compositions can contain, for example, from about 0.5% to about 10% by weight of the postbiotic agent, dispersed in a carrier that comprises clay or a similar substance. Such compositions are usually prepared by dissolving the formulation in a suitable solvent and applying it to a granular carrier which has been pre-formed to the appropriate particle size, in the range of from about 0.5 to about 3 mm. Such compositions may also be formulated by making a dough or paste of the carrier and compound and crushing and drying to obtain the desired granular particle size.

Dusts containing the present compositions are prepared by intimately mixing the postbiotic agent in powdered form with a suitable dusty agricultural carrier, such as kaolin clay, ground volcanic rock, and the like. Dusts can suitably contain from about 1% to about 10% of the packets. They can be applied as a seed dressing or as a foliage application with a dust blower machine.

It is equally practical to apply the present formulation in the form of a solution in an appropriate organic solvent, usually petroleum oil, such as the spray oils, which are widely used in agricultural chemistry.

The postbiotic agent can also be applied in the form of an aerosol composition. In such compositions the packets are dissolved or dispersed in a carrier, which is a pressure-generating propellant mixture. The aerosol composition is packaged in a container from which the mixture is dispensed through an atomizing valve.

Another embodiment is an oil-in-water emulsion, wherein the emulsion comprises oily globules which are each provided with a lamellar liquid crystal coating and are dispersed in an aqueous phase, wherein each oily globule comprises at least one compound which is agriculturally active, and is individually coated with a monolamellar or oligolamellar layer including: (1) at least one non-ionic lipophilic surface-active agent, (2) at least one non-ionic hydrophilic surface-active agent and (3) at least one ionic surface-active agent, wherein the globules having a mean particle diameter of less than 800 nanometers. Further information on the embodiment is disclosed in U.S. patent publication 20070027034 published Feb. 1, 2007.

Additionally, generally, when the molecules disclosed above are used in a formulation, such formulation can also contain other components. These components include, but are not limited to, (this is a non-exhaustive and non-mutually exclusive list) wetters, spreaders, stickers, penetrants, buffers, sequestering agents, drift reduction agents, compatibility agents, anti-foam agents, cleaning agents, and emulsifiers. A few components are described forthwith.

A wetting agent is a substance that when added to a liquid increases the spreading or penetration power of the liquid by reducing the interfacial tension between the liquid and the surface on which it is spreading. Wetting agents are used for two main functions in agrochemical formulations: during processing and manufacture to increase the rate of wetting of powders in water to make concentrates for soluble liquids or suspension concentrates; and during mixing of a product with water in a spray tank to reduce the wetting time of wettable powders and to improve the penetration of water into water-dispersible granules. Examples of wetting agents used in wettable powder, suspension concentrate, and water-dispersible granule formulations are: sodium lauryl sulfate; sodium dioctyl sulfosuccinate; alkyl phenol ethoxylates; and aliphatic alcohol ethoxylates.

A dispersing agent is a substance which adsorbs onto the surface of particles and helps to preserve the state of dispersion of the particles and prevents them from reaggregating. Dispersing agents are added to agrochemical formulations to facilitate dispersion and suspension during manufacture, and to ensure the particles redisperse into water in a spray tank. They are widely used in wettable powders, suspension concentrates and water-dispersible granules. Surfactants that are used as dispersing agents have the ability to adsorb strongly onto a particle surface and provide a charged or steric barrier to reaggregation of particles.

The most commonly used surfactants are anionic, non-ionic, or mixtures of the two types. For wettable powder formulations, the most common dispersing agents are sodium lignosulfonates. For suspension concentrates, very good adsorption and stabilization are obtained using polyelectrolytes, such as sodium naphthalene sulfonate formaldehyde condensates. Tristyrylphenol ethoxylate phosphate esters are also used. Non-ionics such as alkylarylethylene oxide condensates and EO-PO block copolymers are sometimes combined with anionics as dispersing agents for suspension concentrates. In recent years, new types of very high molecular weight polymeric surfactants have been developed as dispersing agents. These have very long hydrophobic 'backbones' and a large number of ethylene oxide chains forming the 'teeth' of a 'comb' surfactant. These high molecular weight polymers can give very good long-term stability to suspension concentrates because the hydrophobic backbones have many anchoring points onto the particle surfaces.

Examples of dispersing agents used in agrochemical formulations are: sodium lignosulfonates; sodium naphthalene sulfonate formaldehyde condensates; tristyrylphenol ethoxylate phosphate esters; aliphatic alcohol ethoxylates; alkyl ethoxylates; EO-PO (ethylene oxide—propylene oxide) block copolymers; and graft copolymers.

An emulsifying agent is a substance which stabilizes a suspension of droplets of one liquid phase in another liquid phase. Without the emulsifying agent the two liquids would separate into two immiscible liquid phases. The most commonly used emulsifier blends contain alkylphenol or aliphatic alcohol with twelve or more ethylene oxide units and the oil-soluble calcium salt of dodecylbenzenesulfonic acid. A range of hydrophile-lipophile balance ("HLB") values from 8 to 18 will normally provide good stable emulsions. Emulsion stability can sometimes be improved by the addition of a small amount of an EO-PO block copolymer surfactant.

A solubilizing agent is a surfactant which will form micelles in water at concentrations above the critical micelle concentration. The micelles are then able to dissolve or solubilize water-insoluble materials inside the hydrophobic part of the micelle. The types of surfactants usually used for solubilization are non-ionics, sorbitan monooleates, sorbitan monooleate ethoxylates, and methyl oleate esters.

Surfactants are sometimes used, either alone or with other additives such as mineral or vegetable oils as adjuvants to spray-tank mixes to improve the biological performance of the postbiotic agent on the target. The types of surfactants used for bioenhancement depend generally on the nature and mode of action of the postbiotic agent. However, they are often non-ionics such as: alkyl ethoxylates; linear aliphatic alcohol ethoxylates; aliphatic amine ethoxylates.

A carrier or diluent in an agricultural formulation is a material added to the postbiotic agent to give a product of the required strength. Carriers are usually materials with high absorptive capacities, while diluents are usually materials with low absorptive capacities. Carriers and diluents are used in the formulation of dusts, wettable powders, granules, and water-dispersible granules.

Organic solvents are used mainly in the formulation of emulsifiable concentrates, oil-in-water emulsions, suspoemulsions, and ultra low volume formulations, and to a lesser extent, granular formulations. Sometimes mixtures of solvents are used. The first main groups of solvents are aliphatic paraffinic oils such as kerosene or refined paraffins. The second main group (and the most common) comprises the aromatic solvents such as xylene and higher molecular weight fractions of C9 and C10 aromatic solvents. Chlorinated hydrocarbons are useful as cosolvents to prevent crystallization of the postbiotic agent when the formulation is emulsified into water. Alcohols are sometimes used as cosolvents to increase solvent power. Other solvents may include vegetable oils, seed oils, and esters of vegetable and seed oils.

Thickeners or gelling agents are used mainly in the formulation of suspension concentrates, emulsions, and suspoemulsions to modify the rheology or flow properties of the liquid and to prevent separation and settling of the dispersed particles or droplets. Thickening, gelling, and anti-settling agents generally fall into two categories, namely water-insoluble particulates and water-soluble polymers. It is possible to produce suspension concentrate formulations using clays and silicas. Examples of these types of materials, include, but are not limited to, montmorillonite, bentonite, magnesium aluminum silicate, and attapulgite. Water-soluble polysaccharides have been used as thickening-gelling agents for many years. The types of polysaccharides most commonly used are natural extracts of seeds and seaweeds or are synthetic derivatives of cellulose. Examples of these types of materials include, but are not limited to, guar gum; locust bean gum; carrageenam; alginates; methyl cellulose; sodium carboxymethyl cellulose (SCMC); hydroxyethyl cellulose (HEC). Other types of anti-settling agents are based on modified starches, polyacrylates, polyvinyl alcohol, and polyethylene oxide. Another good anti-settling agent is xanthan gum.

Microorganisms can cause spoilage of formulated products. Therefore preservation agents are used to eliminate or reduce their effect. Examples of such agents include, but are not limited to: propionic acid and its sodium salt; sorbic acid and its sodium or potassium salts; benzoic acid and its sodium salt; p-hydroxybenzoic acid sodium salt; methyl p-hydroxybenzoate; and 1,2-benzisothiazolin-3-one (BIT).

The presence of surfactants often causes water-based formulations to foam during mixing operations in production and in application through a spray tank. In order to reduce the tendency to foam, anti-foam agents are often added either during the production stage or before filling into bottles. Generally, there are two types of anti-foam agents, namely silicones and non-silicones. Silicones are usually aqueous emulsions of dimethyl polysiloxane, while the non-silicone anti-foam agents are water-insoluble oils, such as octanol and nonanol, or silica. In both cases, the function of the anti-foam agent is to displace the surfactant from the air-water interface.

"Green" agents (e.g., adjuvants, surfactants, solvents) can reduce the overall environmental footprint of crop protection formulations. Green agents are biodegradable and generally derived from natural and/or sustainable sources, e.g., plant and animal sources. Specific examples are: vegetable oils, seed oils, and esters thereof, also alkoxylated alkyl polyglucosides.

In some instances, the postbiotic agent can be freeze-dried or lyophilized. See U.S. Pat. No. 4,311,712. The postbiotic agent can later be reconstituted on contact with water or another liquid. Other components can be added to the lyophilized or reconstituted, for example, other agricultural agents, agriculturally acceptable carriers, or other materials in accordance with the formulations described herein.

Other optional features of the composition include carriers or delivery vehicles that protect the postbiotic agent against UV and/or acidic conditions. In some instances, the delivery vehicle contains a pH buffer. In some instances, the composition is formulated to have a pH in the range of about 4.5 to about 9.0, including for example pH ranges of about any one of 5.0 to about 8.0, about 6.5 to about 7.5, or about 6.5 to about 7.0.

In some instances, the composition includes a bait. The bait can be in any suitable form, such as a solid, paste, pellet or powdered form. The bait can also be carried away by the insect back to a population of said host (e.g., a colony or hive). The bait can then act as a food source for other members of the colony, thus providing an effective amount of a postbiotic agent for a large number of insects and potentially an entire insect colony.

The baits can be provided in a suitable "housing" or "trap." Such housings and traps are commercially available and existing traps can be adapted to include the compositions described herein. The housing or trap can be box-shaped for example, and can be provided in pre-formed condition or can be formed of foldable cardboard for example. Suitable materials for a housing or trap include plastics and cardboard, particularly corrugated cardboard. The inside surfaces of the traps can be lined with a sticky substance in order to restrict movement of the insect once inside the trap. The housing or trap can contain a suitable trough inside which can hold the bait in place. A trap is distinguished from a housing because the insect cannot readily leave a trap following entry, whereas a housing acts as a "feeding station" which provides the insect with a preferred environment in which they can feed and feel safe from predators.

In some instances, the composition includes an attractant (e.g., a chemoattractant). The attractant may attract an adult host or immature host (e.g., larva) to the vicinity of the composition. Attractants include pheromones, a chemical that is secreted by an animal, especially an insect, which influences the behavior or development of others of the same species. Other attractants include sugar and protein hydrolysate syrups, yeasts, and rotting meat. Attractants also can be combined with an active ingredient and sprayed onto foliage or other items in the treatment area.

Various attractants are known which influence host behavior as an insect's search for food, oviposition or mating sites, or mates. Attractants useful in the methods and compositions described herein include, for example, eugenol, phenethyl propionate, ethyl dimethylisobutyl-cyclopropane carboxylate, propyl benszodioxancarboxylate, cis-7,8-epoxy-2-methyloctadecane, trans-8,trans-0-dodecadienol, cis-9-tetradecenal (with cis-11-hexadecenal), trans-11-tetradecenal, cis-11-hexadecenal, (Z)-11,12-hexadecadienal, cis-7-dodecenyl acetate, cis-8-dodecenyul acetate, cis-9-dodecenyl acetate, cis-9-tetradecenyl acetate, cis-11-tetradecenyl acetate, trans-11-tetradecenyl acetate (with cis-11), cis-9,trans-11-tetradecadienyl acetate (with cis-9,trans-12), cis-9,trans-1 2-tetradecadienyl acetate, cis-7,cis-11-hexadecadienyl acetate (with cis-7,trans-11), cis-3,cis-13-octadecadienyl acetate, trans-3,cis-13-octadecadienyl acetate, anethole and isoamyl salicylate. Additionally, means other than chemoattractants may also be used to attract insects, including lights in various wavelengths or colors.

The postbiotic agent can also be incorporated into the medium in which the insect grows, lives, reproduces, feeds, or infests. For example, a postbiotic agent can be incorporated into a food container, feeding station, protective wrapping, or a hive. For some applications the postbiotic agent may be bound to a solid support for application in powder form or in a trap or feeding station. As an example, for applications where the composition is to be used in a trap or as bait for a particular insect, the compositions may also be bound to a solid support or encapsulated in a time-release material. For example, in instances where the insect is a honeybee, the compositions described herein can be administered by delivering the composition to a honeybee hive or at least one habitat where a honeybee grows, lives, reproduces, or feeds. In some instances, the postbiotic agent is formulated in a fog, smoke, or other treatment suitable for application to an insect habitat, e.g., a hive.

In formulations and in the use forms prepared from these formulations, the postbiotic agent may be in a mixture with other agricultural agents or otherwise applied in coincidence with other agricultural agents, such as pesticidal agents (e.g., insecticides, antihelminthics, sterilants, acaricides, nematicides, molluscicides, or fungicides), attractants, plant growth-regulating substances, pollen, sucrose, fertilizers, plant growth regulators, safeners, semiochemicals, or herbicides.

For further information on agricultural formulations, see "Chemistry and Technology of Agrochemical Formulations" edited by D. A. Knowles, copyright 1998 by Kluwer Academic Publishers. Also see "Insecticides in Agriculture and Environment—Retrospects and Prospects" by A. S. Perry, I. Yamamoto, I. Ishaaya, and R. Perry, copyright 1998 by Springer-Verlag.

EXAMPLES

The following is an example of the methods of the invention. It is understood that various other embodiments may be practiced, given the general description provided above.

Example 1: Supplementing Honey Bees with Postbiotics to Increase Bee Fitness

This Example demonstrates the ability to use probiotic bacteria metabolites (postbiotics), such as short chain fatty acids (SCFA) e.g., acetate, propionate, and butyrate, in honey bee feed to enhance their developmental rate, the rate of weight gain, and their maturation.

SCFAs are important bacterial fermentation products of gut bacteria that serve as modulators of key pathways, such as insulin signaling pathways in insects. SCFAs, such as acetate, promote insulin signaling, which in turn controls several processes, such as developmental rate, body size and weight gain, and energy metabolism.

SCFAs also control pathways affecting the levels of vitellogenin in bees. Vitellogenin is a major determinant of honey bee lifespan; its dynamics affect the caste and function of the worker bees in the hive, and the capacity to survive winter weather. Vitellogenin also serves a vital function of acting as the protein storage and buffer in the hives bees and for the hive in general. The hive bees use vitellogenin to produce royal jelly, a proteinaceous diet fed to the queen to produce brood (e.g., eggs, larvae, and/or pupae).

Therapeutic Design:

SCFAs, specifically acetate, propionate, and/or butyrate, are included in the diet of newly emerged bees from a healthy colony of *Apis mellifera* (honey bees) at 0.1%, 0.2%, 0.4%, or 0.8% w/v supplemented in the sterile 50% w/v sucrose solution.

Since the newly emerged bees are germ-free, the direct effect of the SCFAs on the bee health is observed by maintaining the bees in germ-free conditions for the entire span of the experiment. The control group is reared in germ-free conditions and are not supplemented with SCFAs.

To observe the effects of SCFAs in the presence of the native microbiota, both the SCFA treatment and the control group bees are allowed to obtain their natural microbiota from their hive material, and nurse bees and their fecal matter.

Ten replicates are used for both the SCFA and control treatment groups for both the axenic and conventional microbiome groups. Ten bees are used for each replicate. The experiment is repeated three times.

Experimental Design:

Newly emerged bees from a healthy colony of *Apis mellifera* (honey bees) are obtained by removing dark-eyed pupae from capped brood cells with sterilized tweezers and transferring them to sterile plastic boxes at 35° C. till they emerge (Kresnerova, et al., PLoS Biol. 2017 Dec. 12; 15(12):e2003467; and Powell, et al., Proc Natl Acad Sci USA. 2016 Nov. 29; 113(48):13887-13892). Each box of newly emerged bees is provided with sterile 50% w/v sucrose solution and gamma-irradiated (30kGy) bee bread ad libitum.

For the experimental groups that are reared germ-free, the SCFA treatment group is provided with either acetate, propionate or butyrate at 0.1%, 0.2%, 0.4%, or 0.8% w/v supplemented in the sterile 50% w/v sucrose solution. To test the combined effect of the SCFAs, acetate, propionate, and butyrate are combined in equal ratios and supplemented in sterile 50% sucrose solution at 0.1%, 0.2%, 0.4%, or 0.8%. The control treatment group is not provided with any SCFAs in their diet.

For the experimental groups that are reared with their native microbiota, all the newly emerged bees are exposed to their hive material and the homogenates of hindguts of nurse bees from their original hives. The SCFA and the control treatment groups are maintained as described above.

Effect Measurements on Bee's Fitness:

The effect of the SCFAs by themselves or in conjunction with the microbes is measured in multiple ways:

1. The body mass of the bees is measured every day for 10 days to assess the body mass growth rate.

2. The mass of both the midgut and hindgut is measured on day 10 by dissecting the gut with fine forceps, segmenting the gut into the midgut and the hindgut, and weighing each section separately.

3. The presence of each of the SCFA, as well as other TCA intermediate metabolites, such as lactate, succinate, malate and/or formate, is measured in the gut and hemolymph on day 10 as described in (Zheng, et al., Proc Natl Acad Sci USA. 2017 May 2; 114(18):4775-4780). Briefly, 10 µl of the gut contents or the hemolymph are collected and homogenized in 50111 of water. Debris is spun down, the supernatant is filter sterilized using a 0.2 µm filter, acidified in $H_2SO_4$ to a final concentration of 10 mM, and the concentration of each SCFA and other metabolite mentioned above is measured using ion-exclusion chromatography using an HPLC system.

4. The vitellogenin protein content and expression of the gene on Day 10 is measured. The RNA from the bee abdominal contents is extracted. mRNA expression level of the vitellogenin gene is measured using RT-qPCR using primers described in Powell, et al., Proc Natl Acad Sci USA. 2017 May 2; 114(18):4775-4780. The total protein from the bee abdomen is extracted to assess the levels of the vitellogenin protein. Available antibodies (e.g., Amdam, et al, PNAS Feb. 18, 2003. 100 (4) 1799-1802) are used to test the total abdominal protein extract to quantify the proportion of vitellogenin (e.g., by western blot).

The bees, both germ free and with native microbiota, raised on the SCFA supplemented diet are expected to have higher body mass and gut mass accumulation per day compared to bees raised on a diet without the SCFAs. The SCFA levels, specifically the butyrate in the gut and hemolymph, are also expected to be higher in bees fed with the SCFAs as compared to the bees fed with SCFA-free diet. The presence of gut microbes may reduce the differences in metabolite levels between the SCFA and the control diet groups. The vitellogenin content of the bees supplemented with SCFAs is expected to be higher than the control bees without SCFA in their diet. Thus, from the the Example described herein, the presence of microbes that provide SCFAs are expected to increase the levels of vitellogenin in bees as compared to germ-free bees in the control treatment.

OTHER EMBODIMENTS

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

The invention claimed is:

1. A method of increasing the fitness of an insect comprising delivering to the insect a composition comprising a postbiotic agent that comprises one or more short chain fatty acids (SCFAs) each of which is isolated from at least one of a *Bifidobacterium* spp., a *Lactobacillus* spp., a *Lactococcus* spp., or a *Streptococcus* spp.

2. The method of claim 1, wherein the postbiotic agent further comprises an enzyme, a peptide, a teichoic acid, a muropeptide, a polysaccharide, or an organic acid.

3. The method of claim 1, wherein the postbiotic agent is at least 0.1% of the composition.

4. The method of claim 1, wherein the insect is a beneficial insect.

5. The method of claim 4, wherein the insect is a bee.

6. The method of claim 5, wherein the bee is a honeybee.

7. The method of claim 6, wherein the honeybee is *Apis mellifera*.

8. The method of claim 1, wherein the insect is utilized in the production of food for humans and/or feed for animals.

9. The method of claim 8, wherein the insect is a cricket, cicada, grasshopper, ant, caterpillar, or scorpion.

10. The method of claim 1, wherein the insect comprises its native microbiota prior to delivery of the composition.

11. The method of claim 1, wherein the method further comprises pre-treating the insect with a probiotic microbial agent.

12. The method of claim 1, wherein the method is effective to increase the fitness of the insect relative to an untreated insect.

13. The method of claim 12, wherein the increase in fitness is an increase in developmental rate, body size, body mass, or nutritional profile of the insect relative to the untreated insect.

14. The method of claim 12, wherein the increase in fitness is an increase in vitellogenin protein in the insect, an increase in vitellogenin gene production in the insect, or a combination thereof, relative to the untreated insect.

15. The method of claim 1, wherein the composition is delivered to the insect to at least one habitat where the insect grows, lives, feeds, or reproduces.

16. The method of claim 1, wherein the composition is a liquid, a solid, an aerosol, a paste, a gel, or a gas composition.

17. The method of claim 1, wherein the postbiotic agent is formulated in a carrier.

18. The method of claim 17, wherein the carrier comprises a nanoparticle, a lipid membrane, an attenuated bacteria, or a plant.

19. The method of claim 1, wherein the composition is delivered as an insect comestible composition for ingestion by the insect.

20. The method of claim 1, wherein the composition is delivered to the insect by ingestion, infusion, injection, smoking, fogging, or spraying.

21. The method of claim 1, wherein the composition comprises an agriculturally acceptable carrier.

* * * * *